United States Patent
Monblanc et al.

(10) Patent No.: US 6,942,835 B2
(45) Date of Patent: Sep. 13, 2005

(54) DEVICE FOR HOLDING A SOLID IN A TUBE, AND TEST KIT USING SUCH A DEVICE

(75) Inventors: Philippe Monblanc, Mauguio (FR); Bruno Lacan, Clermont L'Herault (FR)

(73) Assignee: Contralco, Gignac (FR)

( * ) Notice: Subject to any disclaimer, the term of this patent is extended or adjusted under 35 U.S.C. 154(b) by 552 days.

(21) Appl. No.: 10/042,615

(22) Filed: Jan. 8, 2002

(65) Prior Publication Data

US 2002/0110497 A1 Aug. 15, 2002

(30) Foreign Application Priority Data

Jan. 19, 2001 (FR) .............................. 01 00733

(51) Int. Cl.⁷ .............................................. B01N 35/00
(52) U.S. Cl. ........................... 422/61; 422/99; 422/101; 422/104; 436/175; 436/177; 436/808; 210/455; 210/477; 210/480
(58) Field of Search ............................ 422/61, 83, 102, 422/104, 101; 436/808, 900, 174, 175, 177–178; 210/232, 323.1, 435, 450, 454, 455, 460, 477, 480, 482

(56) References Cited

U.S. PATENT DOCUMENTS

| 1,967,811 A | * | 7/1934 | Cory ........................... 99/292 |
| 2,982,377 A | | 5/1961 | Eames |
| 3,411,629 A | | 11/1968 | Wilber et al. |
| 3,870,492 A | | 3/1975 | Guild |
| 4,080,170 A | * | 3/1978 | Borkenstein ................ 436/178 |
| 4,350,037 A | | 9/1982 | Higham |
| 4,740,475 A | * | 4/1988 | Paul .......................... 436/165 |
| 5,922,608 A | * | 7/1999 | Farnsworth et al. .......... 436/89 |

FOREIGN PATENT DOCUMENTS

| DE | 3 539 446 A1 | 7/1986 |
| FR | 2 484 283 A1 | 12/1981 |

* cited by examiner

Primary Examiner—Lyle A. Alexander
(74) Attorney, Agent, or Firm—Townsend and Townsend and Crew LLP

(57) ABSTRACT

The invention provides a test kit, having a tube (17) and a reactant (30) which is held between two holding devices (8, 9). Each holding device has a filter (10), with an elastically deformable part (13) transverse to a disc (11), and a spring (15) which presses the elastically deformable part (13) against the walls of the tube (17).

14 Claims, 1 Drawing Sheet

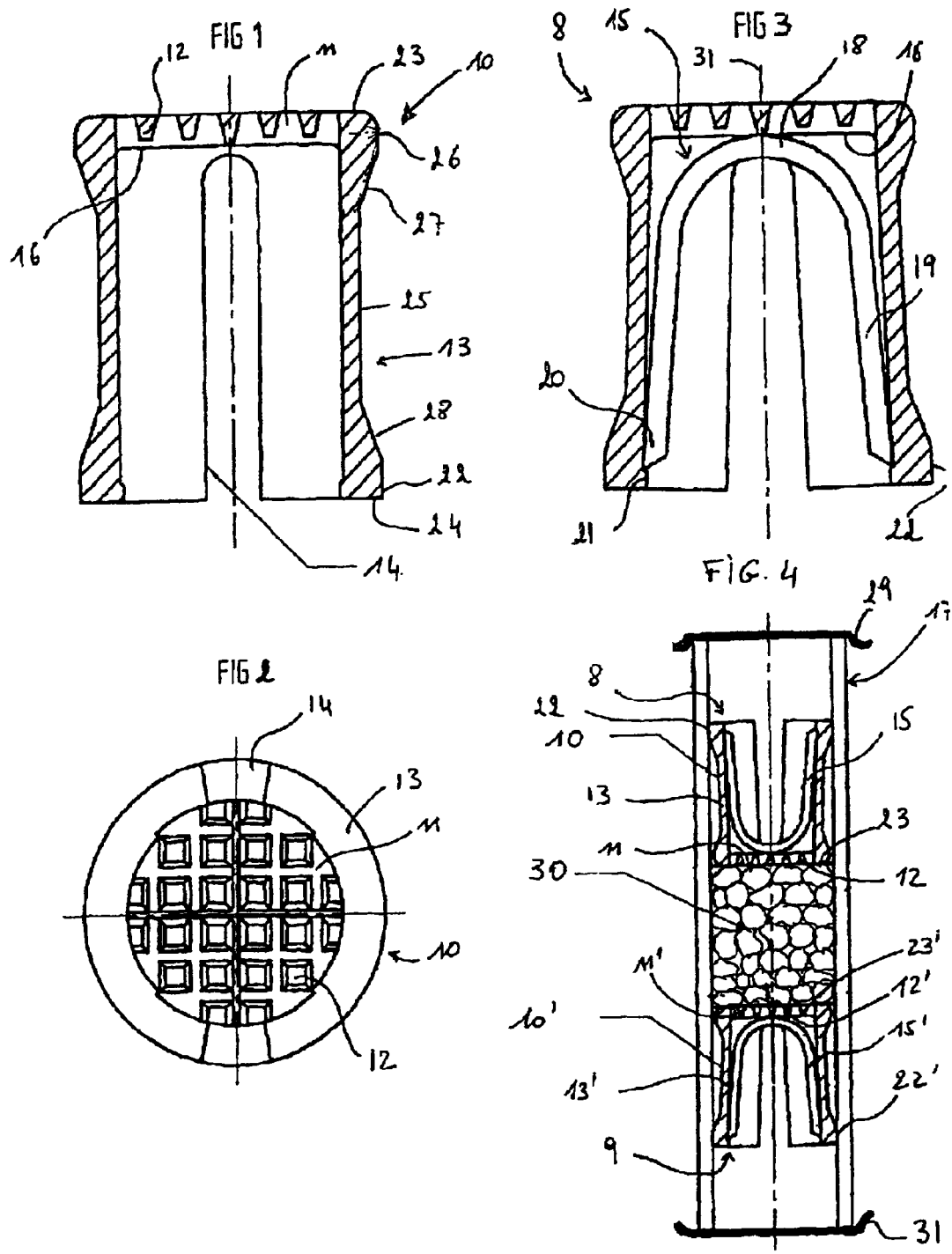

DEVICE FOR HOLDING A SOLID IN A TUBE, AND TEST KIT USING SUCH A DEVICE

The present invention relates to devices used for detecting the presence of a given substance in a fluid, and more specifically to the containers holding a reactant which is sensitive to the presence of the substance, such as breathalysers for example.

The presence of a substance in a fluid is detected by making the fluid liable to contain the substance come into contact with a reactant which reacts with the substance to be detected; the detected content of substance in the fluid depends on the amount of reactant which has reacted on contact with the substance. The quality of the measurement by the device is therefore closely linked to the position of the reactant in the container. As an example, the present invention may be used in a breathalyser for measuring the presence and, if necessary, the amount of ethyl alcohol in the air expelled by a person. A breathalyser is composed, firstly, of a balloon to be filled with air and, secondly, of a tube containing a reactant sensitive to the presence of ethyl alcohol. The operation of a breathalyser is as follows: the person of whom it is desired to check the alcohol level blows into the balloon through a nozzle so as to fill it completely. The tube containing the alcohol-sensitive reactant is then inserted into the nozzle and the balloon is pressed so as to slowly and completely empty it through the tube containing the reactant. If the expelled air has an ethyl alcohol content greater than a certain value, the reactant indicates this, for example by a colour change. In addition, a gauge line made on the tube, at a certain level with respect to the reactant, makes it possible to know if the alcohol content calibration threshold has been exceeded. The reactant must therefore, on the one hand, be suitably compacted so as to allow the air to flow through the reactant and, on the other hand, the position of the reactant must be invariant with respect to the gauge line in order to compare the alcohol content with the calibration threshold.

Various solutions have been proposed for positioning and holding the reactant. Document FR-A-2 497 954 discloses a device used for detecting the presence of a substance in a fluid by recommending that the fluid flow in a plastic tube through a granulated reactant. The plastic tube has, at one of its ends, a transverse partition moulded with the tube. After the granulated reactant has been inserted into the tube, the latter is closed by a plastic plug which has perforations and is moulded as one piece with a transverse disc and a deformable ring interposed between the disc and the plug. The disc compacts the granules against the transverse partition by means of the force generated by deformation of the ring. However, some reactants oxidize on contact with air and, since the plastic tube is not sufficiently airtight, the assembly must be kept in a glass container closed by a cap in order to protect the granules from oxidation.

To detect the presence and to measure the content of a substance in a fluid, the devices currently available on the market (Red Line, Dräger, Mesir, etc.) make a fluid flow in a tubular glass body through a granulated reactant held by two metal grids inserted into the tube. Since the tolerances on the inside diameter of the glass tubes used are from 3 to 4 tenths of a millimeter, the force retaining the metal grids in the tube varies widely. If the diameter of the glass tube is at the upper tolerance level, the force retaining the metal grids in the glass tube is at a minimum, which poses two problems:

when assembling the device, if a constant force is applied to the grid in order to position it, the compacting of the reactant is at a maximum, which results in compression and then degradation of the granules and therefore variations in the reaction during use (colour intensity, amplitude and rate);

when the device is subjected to shocks or vibrations, the grids move in the glass tube and no longer fulfil their function of holding and positioning the reactant.

If the diameter of the glass tube is at the lower tolerance level, the force retaining the metal grids in the glass tube is at a maximum, which poses two problems:

when inserting the metal grids into the glass tube, these bend and there is a major risk of the glass tube being damaged or broken;

when assembling the device, if a constant force is applied to the grid in order to position it, the reactant is not sufficiently compacted. This results in variations in the reaction during use (colour intensity, amplitude and rate).

In addition, the grid does not ensure a uniform flow of fluid over the entire area of contact with the reactant, nor is the flow reproducible from one grid to another. This generates emanations, of random position and random amplitude, reducing the precision of the measurement.

There is consequently a need to have a device which makes it possible to position and hold a solid reactant in a tube for detecting the presence and for measuring the content of a substance in a fluid. To do this, the invention relates to a device for holding a solid in a tube, comprising:

a filter having an elastically deformable part transverse to a disc; and a spring pressing the elastically deformable part against the walls of the tube.

In one embodiment, the disc has transverse apertures.

In another embodiment, the elastically deformable part is in the form of a tube with a slit over part of its length.

In another embodiment, the elastically deformable part comprises two tabs.

The invention also relates to a test means comprising:

a tube;

two holding devices; and a reactant between the ends of the holding devices.

The tube of the test means is, for example, made of glass. In one embodiment, the reactant is in the form of granules. The faces of the discs have transverse apertures smaller than the size of the granules.

In one embodiment, the test means includes a cap which closes off the tube at each of its ends.

In another embodiment, the diameter of the ends of the holding devices is at most equal to the inside diameter of the tube.

The invention also relates to a method of assembling a test means, comprising the steps of:

introducing a holding device into a tube;

introducing a reactant into the tube; and introducing a second holding device into the tube.

In one embodiment, the method furthermore includes the step of closing off the tube with a cap at each of its ends.

BRIEF DESCRIPTION OF THE DRAWINGS

Further features and advantages of the invention will become apparent on reading the following detailed description of embodiments of the invention, these being given purely by way of example and with reference to the drawings, in which:

FIG. 1 shows a filter in cross section;

FIG. 2 shows a bottom view of the filter of FIG. 1;

FIG. 3 is a cross section through a holding device according to one embodiment of the invention; and FIG. 4 shows a cross section through a test means for detecting a substance in a fluid.

In the description which follows, the term "holding device" denotes the elements for preventing a solid body in a predetermined place from moving along a tube. The solid body prevented from moving by the holding device may be a compact solid body or may be in the form of powder or granules. The term "tube" denotes a means of confining the said solid body, through which a fluid flows for the purpose of detecting a substance in the fluid.

The invention relates to a holding device placed inside a tube. It comprises a filter and a spring. The filter has a disc, such as a grid for example, and an elastically deformable part which extends transversely with respect to a surface of the disc in one direction. The filter has a diameter at the disc at most equal to the inside diameter of the tube. A spring is placed inside the elastically deformable part so as to press the latter against the walls of the tube and prevent the filter from moving along the tube. It is then possible to fill the tube with a solid body which is retained on each side by a holding device, the latter allowing, however, a fluid to flow through the filter.

FIG. 1 shows, in cross section, a filter 10 having an elastically deformable part 13 of tubular shape. One of the ends 23 of the filter is closed off by a disc 11, the other end 24 being left open. The disc 11 is, for example, a grid. The filter 10 is made, by injection or compression moulding, of a material giving the structure rigidity, preferably a plastic (for example, polystyrene or PVC). The elastically deformable part 13 may thus be elastically deformed when its walls are pinched together or moved apart. The position shown in FIG. 1 is the rest position.

In the example in FIG. 1, the elastically deformable part 13 is a tube partially slit in the length direction. The elastically deformable part 13 is approximately perpendicular to the disc 11.

FIG. 2 shows a bottom view of a filter 10 of FIG. 1. The elastically deformable part 13 has one of its ends 23 closed off by a disc 11 provided with perforations 12. In the example of FIG. 2, the perforations in the disc 11 are distributed over the surface of the disc 11 so that the latter forms a grid allowing a fluid to flow homogeneously through the filter over the entire surface of the disc 11. The filter has two diametrically opposed slits 14 made axially over part of the walls of the elastically deformable part 13 starting from its end 24. A larger number of slits may be provided so as to make the elastically deformable part 13 less rigid.

FIG. 3 shows a cross section through a holding device 8 which includes the filter 10 and of which device the end 23 of the elastically deformable part 13 is closed off by the disc 11. A spring 15 is placed in the filter, thus splaying the walls of the elastically deformable part 13. The spring is preferably made of metal so as to exert a constant deformation force on the elastically deformable part 13. In the example of FIG. 3, the spring 15 is a U-shaped piece placed inside the filter 10. The base 18 of the spring 15 rests against the surface 16 of the disc 11 from which the elastically deformable part 13 projects. The ends 20 of the branches 19 of the spring 15 rest on a shoulder 21 made on the inside face of the elastically deformable part 13. The shoulder 21 is made at a certain distance from the disc 11 so that the spring 15 is prevented from moving axially in translation and its ends 20 press on the filter 10 at its free end 24. The shoulder 21 may be annular so as to make it easier for the spring 15 to be positioned angularly about the axis 31 of the filter 10.

When the spring 15 is inserted into the filter 10, the walls of the filter undergo radial deformation. The radial deformation is greater the further away from the end 23. The inside diameter of the elastically deformable part 13 at the end 24 becomes greater than that of the end 23 closed off by the grid 11. The spring 15 deforms the filter 10 for the purpose of positioning the latter inside a container, such as a tube. In FIG. 1, the outer casing of the filter 10 has two frustoconical surfaces 27, 28 flaring out slightly towards the ends 23, 24 which terminate in two annular regions 22, 26. The outside diameter of the annular regions 22, 26 of the filter 10 is greater than the outside diameter of a part 25 located between these annular regions 22, 26. The outside diameter of the filter may be constant over the entire length.

FIG. 4 shows a tube 17 in which two holding devices 8 and 9 according to the invention are placed so as to prevent a body 30 in a predetermined location from moving. The outside diameter of the holding devices 8, 9 is less than the inside diameter of the tube 17 so that the holding devices 8, 9 slide freely inside the tube 17. When the springs 15, 15' are in the filters 10, 10' respectively, the walls of the filters 10, 10' are moved apart and pressed against the walls of the tube 17. The holding devices 8, 9 are then prevented from moving axially in the tube 17. Provision may be made for only the annular region 22, 22' to be in contact with the wall of the tube 17 so as to press on the walls of the filters 10, 10' in the region where their deformation is greatest so that the force needed for the useful deformation of the elastically deformable part 13, 13' of the filters 10, 10' is negligible. The springs 15, 15' are designed so that their force remains constant within the tolerance ranges of the tube. The force retaining the holding devices 8, 9 in the tube 17 may be adjusted to 350±50 g, which makes it possible for repeated and controlled holding and compacting of the body 30. This value is the force needed to move one of the holding devices inside the tube.

The holding device 8 is introduced into the tube 17 in the following manner. The spring 15 is inserted into the filter 10 so as to splay out the walls of the filter 10. The filter 10 thus deformed is introduced into the tube 17, starting with the end 23. At this end, the outside diameter of the holding device 8 is less than that of the tube 17. As the holding device 8 is pushed in further, its outside diameter gradually becomes larger than the inside diameter of the tube 17, because of the deformation by the spring 15. By applying a greater pressure on the end 24, the frustoconical surface 28 engages with an edge of the tube 17. A force counter to the deformation force of the means 15 moves the walls of the holding device 8 back towards the rest position, thus allowing the holding device to be fully inserted into the tube 17. It is possible to continue to exert a pressure on the end 24 so as to bring the holding device 8 into its final position along the tube 17. The holding device 8 is prevented from moving in translation along the axis of the tube 17 because of the deformation force of the spring 15 pressing the region 22 against the walls of the tube 17.

The holding device 8 may be used to hold a body 30 in the tube 17. A first holding device 8 is firstly introduced into the tube 17 in the manner described above. The body 30, having dimensions enabling it to enter the tube, is then deposited in the latter against the disc 11, on that side from which the elastically deformable part 13 does not project. A second holding device 9 is then introduced into the tube 17 in the manner described above, but via the opposite side of the tube 17 from that via which the first holding device 8 was introduced. The two holding devices 8, 9 have their ends 23, 23' facing each other, the body 30 being interposed between the two discs 11, 11'. The body 30 is held in its position by the deformation of the elastically deformable part 13, 13' of each of the holding devices 8, 9 because of the forces exerted by the springs 15, 15'.

The deformation forces exerted by the springs 15, 15' for preventing the holding devices 8, 9 from moving along the tube 17 are sufficient to prevent the filter and the body 30, in position, from moving. In the situation in which the body 30 is a powder or granules, the size of the perforations 12, 12' in the discs 11, 11' is such that the particles of the body 30 do not pass through the disc, but the fluid is able to flow through the assembly. The diameter of the holding devices 8, 9 in their annular region 26 and 26' is at most equal to the inside diameter of the tube 17. The diameter of the holding devices 8, 9 may be less than the inside diameter of the tube 17, but such that the body 30, in a form of granules or powder, cannot pass between the walls of the tube 17 and the annular regions 26 and 26' of the holding devices 8, 9.

The filter 10 may, for example, be used in a breathalyser tube for measuring the presence and, if necessary, the content of ethyl alcohol in the air expelled by a person. If the expelled air has an ethyl alcohol content greater than a certain value, the reactant indicates this, for example by a colour change. A gauge line made on the tube, at a certain level with respect to the reactant, makes it possible to know if the calibration threshold has been exceeded. The holding device according to the invention makes it possible, on the one hand, for the reactant to be suitably compacted so as to allow the air to flow through the reactant and to ensure, on the other hand, that the position of the reactant is invariant with respect to the gauge line.

The reactant used is, for example, silica gel impregnated with a sulphochromic solution in the form of granules which are sensitive to contact with air. It is held in the tube 17 between two holding elements 10, 10' according to the invention. The diameter of the discs 11, 11' is such that the granules cannot pass between the discs and the walls of the tube; nor can the granules, which are friable and toxic, be jammed between the discs 11, 11' and the walls of the tube 17 so as to prevent degradation of the reactant possibly causing, on the one hand, a variation in the reaction and, on the other hand, passage of the degraded granules through the discs 11, 11'.

Using the holding device in a breathalyser tube allows the tube 17 containing the reactant 30 to be packaged more easily, it being possible for the tube 17 to be closed by a cap 29, 31 at each of its ends. The cap is, for example, a disc bonded to each of the ends of the tube. The caps 29, 31 are then punctured or torn off each of the ends in order to use the tube in a breathalyser test.

The invention is not limited to the embodiments described above purely by way of illustration.

For example, according to another embodiment, the filter 10 has an elastically deformable part 13 which is transverse to the disc 11 but is not perpendicular to it. The elastically deformable part 13 flares out as one goes further away from the disc 11, in such a way that the end 23 of the filter has an outside diameter greater than the inside diameter of the tube 17. The filter 10 is then deformed by pinching as it is introduced into the tube 17 and its walls are pressed against the walls of the tube 17 so as to prevent the filter 10 from moving along the tube 17. The spring 15 then presses the elastically deformable part 13 against the walls of the tube 17 in order to prevent the said elastically deformable part from creeping and to prevent the filter 10 from moving along the tube 17.

In yet another embodiment, the elastically deformable part 13 consists of two or more tabs which are pressed against the walls of the tube 17 by the spring 15.

In yet another embodiment, the perforations 12 may be cylindrical in shape, with a staggered distribution.

What is claimed is:

1. A holding device for holding a solid in a tube, comprising:
    a filter having an elastically deformable part that is coupled to a disk such that the deformable part is transverse to the disc and wherein the disc and the deformable part are a continuous piece of the same material;
    a spring pressing the elastically deformable part of said filter against the walls of the tube; and
    a reactant disposed within the tube.

2. A holding device according to claim 1, characterized in that the disc has transverse apertures.

3. A holding device according to claim 1, characterized in that the part is in the form of a tube with a slit over part of its length.

4. A holding device according to claim 1, characterized in that the part includes two slits.

5. A test kit comprising:
    a tube;
    two holding devices according to claim 1; and
    a reactant between the ends of the holding devices of claim 1.

6. The test kit according to claim 5, characterized in that the tube is made of glass.

7. The test kit according to claim 5, characterized in that the reactant is in the form of granules.

8. The test kit according to claim 7, characterized in that the discs have transverse apertures smaller than the size of the granules.

9. The test kit according to claim 5, characterized in that a cap closes off the tube at each of its ends.

10. The test kit according to claim 5, characterized in that the diameter of the ends is at most equal to the inside diameter of the tube.

11. A method of assembling a test kit according to claim 5, comprising the steps of:
    introducing the holding device of claim 1 into a tube;
    introducing a reactant into the tube; and
    introducing a second holding device into the tube.

12. A method according to claim 11, characterized in that it furthermore includes the step of closing off the tube with a cap at each of its ends.

13. A test kit comprising:
    a tube;
    two holding devices that each comprise a filter having an elastically deformiable part transverse to a disc, wherein the disc and the deformiable part are a continuous piece of the same material, and a spring pressing the elastically deformable part of said filter against the walls
    of the tube; and
    a reactant between the ends of the holding devices.

14. A method of assembling a test kit, comprising the steps of:
    providing a first holding device comprising a filter having an elastically deformable part transverse to a disc, wherein the disc and the deformable part are a continuous piece of the same material and a spring pressing the elastically deformable part of said filter against the walls of the tube;
    introducing the first holding device into a tube;
    introducing a reactant into the tube; and
    introducing a second holding device into the tube.

* * * * *